US012605364B2

(12) United States Patent
Hepner

(10) Patent No.: US 12,605,364 B2
(45) Date of Patent: Apr. 21, 2026

(54) METHODS OF TREATING SARS-CoV-2 INFECTIONS

(71) Applicant: EAGLE PHARMACEUTICALS, INC., Woodcliff Lake, NJ (US)

(72) Inventor: Adrian Hepner, Woodcliff Lake, NJ (US)

(73) Assignee: Eagle Pharmaceuticals, Inc., Woodcliff Lake, NJ (US)

( * ) Notice: Subject to any disclaimer, the term of this patent is extended or adjusted under 35 U.S.C. 154(b) by 768 days.

(21) Appl. No.: 17/995,602

(22) PCT Filed: Apr. 8, 2021

(86) PCT No.: PCT/US2021/026302
§ 371 (c)(1),
(2) Date: Oct. 6, 2022

(87) PCT Pub. No.: WO2021/207443
PCT Pub. Date: Oct. 14, 2021

(65) Prior Publication Data

US 2023/0144719 A1 May 11, 2023

Related U.S. Application Data

(60) Provisional application No. 63/062,599, filed on Aug. 7, 2020, provisional application No. 63/008,486, filed on Apr. 10, 2020.

(51) Int. Cl.
*A61K 31/4178* (2006.01)
*A61P 31/14* (2006.01)

(52) U.S. Cl.
CPC .......... *A61K 31/4178* (2013.01); *A61P 31/14* (2018.01)

(58) Field of Classification Search
None
See application file for complete search history.

(56) References Cited

FOREIGN PATENT DOCUMENTS

| | | |
|---|---|---|
| WO | 2019/079721 A1 | 4/2019 |
| WO | 2019/095056 A1 | 5/2019 |
| WO | 2019/175761 A1 | 9/2019 |

OTHER PUBLICATIONS

Wu et al. Analysis of therapeutic targets for SARS-CoV-2 and discovery of potential drugs by computational methods. Acta Pharmaceutica Sinica B 2020; 10(5): 766-788 (available online Feb. 27, 2020). (Year: 2020).*
Clark, K.B. Biotic activity of Ca2+-modulating non-traditional antimicrobial and—viral agents. Front. Microbiol. 4:381 (2013). (Year: 2013).*
Kajani et al., "Neuroleptic malignant syndrome in a COVID-19 patient", Brain, Behavior, and Immunity, vol. 88, May 18, 2020, pp. 28-29.
'Five me the calcium!' Tulane virus takes over cellular calcium signaling to replicate, ScienceDaily, Baylor College of Medicine, Nov. 2019, 5 pages.
Chami, Cytobiological consequences of calcium-signaling alterations induced by human viral proteins, ScienceDirect, Biochimica et Biophysica Acta 1763, 2006, 1344-1362.
Jiang B et al: "Could dantrolene be explored as a repurposed drug to treat COVID-19 patients by restoring intracellular calcium homeostasis?", European review for medical and pharmacological sciences, Oct. 1, 2020 (Oct. 1, 2020), pp. 10228-10238, XP055812019, Italy DOI: 10.26355/eurrev_202010_23247.
Krause T. et al: "Dantrolene? A review of its pharmacology, therapeutic use and new developments", Anaesthesia., vol. 59, No. 4, Apr. 1, 2004 (Apr. 1, 2004), pp. 364-373, XP055812041 ,GBISSN: 0003-2409, DOI: 10.1111/j.1365-2044.2004.03658.x.
Nieto-Torres Jose L. et al: "Severe acute respiratory syndrome coronavirus E protein transports calcium ions and activates the NLRP3 inflammasome", Virology, vol. 485, Nov. 1, 2015 (Nov. 1, 2015), pp. 330-339, XP055812387,Amsterdam, NLISSN: 0042-6822, DOI: 10.1016/j.viroL2015.08.010.
Reed & Muench, American Journal of Hygiene. 27: 493-497 (1938).
Straus Marco R. et al: "Ca2+ ions promote fusion of Middle East Respiratory Syndrome coronavirus with host cells and increase infectivity",bioRxiv, Dec. 19, 2019 (Dec. 19, 2019), XP055812235,DOI: 10.1101/2019.12.18.881391 [retrieved on Jun. 9, 2021].
Tang et al., Coronavirus membrane fusion mechanism offers as a potential target for antiviral development, Antiviral Research, 178, 2020, 104792.
World Health Organization, Laboratory Procedures, Serological Detection of avian influenza A(H7N9) infections by microneutralization assay, May 2013, 1-15.
Chandel et al., "Structure based drug repurposing through targeting Nsp9 replicase and Spike Proteins of SARS-CoV-2", ChemRxiv, 2020, pp. 1-28.

* cited by examiner

*Primary Examiner* — Jeffrey S Lundgren
*Assistant Examiner* — Sara Elizabeth Townsley
(74) *Attorney, Agent, or Firm* — BakerHostetler

(57) ABSTRACT

The disclosure is directed to methods of using dantrolene or a dantrolene prodrug, or a pharmaceutically acceptable salt thereof, to treat COVID-19 and SARS-CoV-2 infections.

24 Claims, No Drawings

METHODS OF TREATING SARS-CoV-2 INFECTIONS

CROSS REFERENCE TO RELATED APPLICATIONS

This application is a National Stage Application filed under 35 U.S.C. 371 of International Application No. PCT/US2021/026302, filed Apr. 8, 2021, which claims priority to and the benefit of U.S. Provisional Patent Application No. 63/008,486, filed Apr. 10, 2020 and U.S. Provisional Patent Application No. 63/062,599, filed Aug. 7, 2020, the disclosure of which is incorporated herein by reference in its entirety.

TECHNICAL FIELD

The disclosure is directed to methods of using dantrolene or a dantrolene prodrug, or a pharmaceutically acceptable salt thereof, to treat COVID-19 and SARS-CoV-2 infections.

BACKGROUND

Worldwide progression of Severe Acute Respiratory Syndrome Coronavirus 2 (SARS-CoV-2) has led to a rapid increase in the number of cases of Coronavirus Disease 2019 (COVID-19). The recently identified coronavirus SARS-CoV-2 poses a threat to worldwide public health. Treatments effective to treat this new virus are urgently needed.

SUMMARY

The disclosure is directed to methods of treating COVID-19 in a subject comprising administering to the subject dantrolene or a pharmaceutically acceptable salt thereof or by administering a dantrolene prodrug or a pharmaceutically acceptable salt thereof.

The disclosure is also directed to methods for inhibiting replication of SARS-CoV-2 in a subject comprising administering to the subject dantrolene, or a pharmaceutically acceptable salt thereof or by administering a dantrolene prodrug or a pharmaceutically acceptable salt thereof.

The disclosure is also directed to methods for inhibiting replication of SARS-CoV-2 in a host cell comprising administering to the host cell dantrolene, or a pharmaceutically acceptable salt thereof or by administering a dantrolene prodrug or a pharmaceutically acceptable salt thereof.

The disclosure is also directed to methods for reducing the infectivity of SARS-CoV-2 by administering to a host cell dantrolene, or a pharmaceutically acceptable salt thereof or by administering a dantrolene prodrug or a pharmaceutically acceptable salt thereof.

DETAILED DESCRIPTION OF ILLUSTRATIVE EMBODIMENTS

The present disclosure may be understood more readily by reference to the following detailed description taken in connection with the accompanying figures and examples, which form a part of this disclosure. It is to be understood that this disclosure is not limited to the specific compositions, devices, methods, applications, conditions, or parameters described and/or shown herein, and that the terminology used herein is for the purpose of describing particular embodiments by way of example only and is not intended to be limiting of the claimed disclosure.

As used in the specification including the appended claims, the singular forms "a," "an," and "the" include the plural, and reference to a particular numerical value includes at least that particular value, unless the context clearly dictates otherwise.

When a range of values is expressed, an exemplary embodiment includes from the one particular value and/or to the other particular value. All ranges are inclusive and combinable. Further, reference to values stated in ranges includes each and every value within that range. When values are expressed as approximations, by use of the preposition "about," it will be understood that the particular value forms another embodiment. The term "about" as used herein when referring to a measurable value such as an amount, a temporal duration, and the like, is meant to encompass reasonable variations of the value, such as, for example, ±10% from the specified value. For example, the phrase "about 50%" can include ±10% of 50, or from 45% to 55%, inclusive of 50%.

It is to be appreciated that certain features of the disclosure which are, for clarity, described herein in the context of separate embodiments, may also be provided in combination in a single embodiment. Conversely, various features of the disclosure that are, for brevity, described in the context of a single embodiment, may also be provided separately or in any subcombination.

As used herein, whether by itself or in conjunction with another term or terms, it should be understood that the phrases "method of treating" and "method of treatment" may be used interchangeably with the phrase "for use in the treatment of" a particular disease.

As used herein, whether by itself or in conjunction with another term or terms, "pharmaceutically acceptable" indicates that the designated entity such as, for example, a pharmaceutically acceptable excipient, is generally chemically and/or physically compatible with other ingredients in a composition, and/or is generally physiologically compatible with the recipient thereof.

As used herein, whether by themselves or in conjunction with another term or terms, "subject(s)," "individual(s)," and "patient(s)", refer to mammals, including humans. The term human(s) refers to and includes, a human child, adolescent, or adult.

As used herein, whether by themselves or in conjunction with another term or terms, "treats," "treating," "treated," and "treatment," refer to and include ameliorative, palliative, and/or curative uses and results or any combination thereof. In other embodiments, the methods described herein can be used prophylactically. It should be understood that "prophylaxis" or a prophylactic use or result do not refer to nor require absolute or total prevention (i.e., a 100% preventative or protective use or result). As used herein, prophylaxis or a prophylactic use or result refers to uses and results in which administration of a compound or composition diminishes or reduces the severity of a particular condition, symptom, disorder, or disease described herein; diminishes or reduces the likelihood of experiencing a particular condition, symptom, disorder, or disease described herein; or delays the onset or relapse (reoccurrence) of a particular condition, symptom, disorder, or disease described herein; or any combination of the foregoing.

As used herein, whether used alone or in conjunction with another term or terms, "therapeutic" and "therapeutically effective amount" refer to an amount of a compound or composition that (a) treats a particular condition, symptom, disorder, or disease described herein; (b) attenuates, ameliorates, or eliminates one or more symptoms of a particular condition, disorder, or disease described herein; (c) delays the onset or relapse (reoccurrence) of a particular condition, symptom, disorder, or disease described herein. It should be understood that the terms "therapeutic" and "therapeutically effective" encompass any one of the aforementioned effects (a)-(c), either alone or in combination with any of the others (a)-(c).

As used herein, a "host cell" is, for example, an epithelial cell, for example, a pulmonary epithelial cell, for example, a mammalian pulmonary epithelial cell such as a human pulmonary epithelial cell. Other host cells include white blood cells, for example, macrophages and T-cells.

As used herein, "normalization of fever" is reduction of a subject's temperature to <36.6° C. armpit, <37.2° C. oral, or <37.8° C. rectal, sustained for at least 24 hours.

As used herein, "normalization of oxygen saturation" is an increase in a subject's peripheral capillary oxygen saturation (SpO2) >94%, sustained for at least 24 hours.

As used herein, "inhibiting replication of SARS-CoV-2" refers to decreasing viral load of SARS-CoV-2. Methods for determining SARS-CoV-2 replication inhibition can be determined by those skilled in the art.

Dantrolene is approved for treating malignant hyperthermia and preventing malignant hyperthermia in high-risk patients Malignant hyperthermia is a condition that predisposes susceptible individuals to a life-threatening adverse reaction upon exposure to potent volatile anesthetics (halothane, isoflurane, sevoflurane, desflurane, etc.) and the skeletal muscle relaxant succinylcholine. The anesthetic drugs trigger an uncontrolled $Ca^{2+}$ release from the endoplasmic reticulum (ER) through the ryanodine receptors (RyR) causing a rapid and sustained rise in myoplasmic $Ca^{2+}$. Administration of dantrolene reestablishes cellular calcium homeostasis by inhibiting the release channels in the ER, resulting in lower levels of intracellular $Ca^{2+}$.

RYANODEX (dantrolene sodium, 250 mg/vial) is approved for treating malignant hyperthermia and for preventing malignant hyperthermia in high-risk patients. RYANODEX forms an aqueous nanosuspension for IV injection containing dantrolene 50 mg/mL upon reconstitution with 5 mL of USP sterile water for injection (WFI) (without a bacteriostatic agent). Dissolution of RYANODEX suspension in human plasma is extremely rapid, achieving complete dissolution within 1 minute.

Dantrolene is a surprisingly effective treatment for SAR-CoV-2 infection. Dantrolene can decrease the virus' ability to replicate, mature, create virions, release from cells, and/or infect other cells.

Methods of the disclosure can also be accomplished using dantrolene prodrugs, and pharmaceutically acceptable salts thereof. Exemplary dantrolene prodrugs are described in WO2019/079721, the entirety of which is incorporated by reference herein.

Preferred dantrolene prodrugs include, for example, compounds of formula I

I

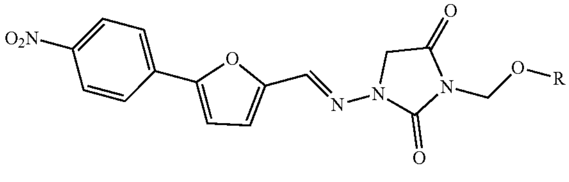

wherein R is —$P(O)(OH)_2$ or —$P(O)(OR_1)(OR_2)$; $R_1$ is H, —$C_{1-26}$alkyl, aryl, $C_{1-6}$alkC(O)O—$C_{1-26}$alkyl, —$C_1$alkOC(O)$C_{1-26}$alkyl, or $C_1$alkOC(O)O$C_{1-26}$alkyl; and $R_2$ is —$C_{1-26}$alkyl, aryl, $C_{1-6}$alkC(O)O—$C_{1-26}$alkyl, —$C_1$alkOC(O)$C_{1-26}$alkyl, or $C_1$alkOC(O)O$C_{1-26}$alkyl, as well as pharmaceutically acceptable salts thereof. Particularly preferred compounds of formula I include compounds 2 and 2a:

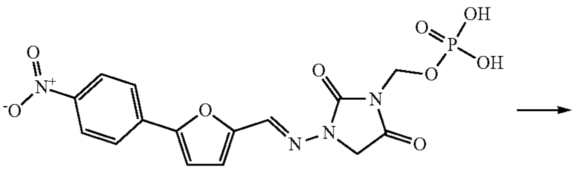

2

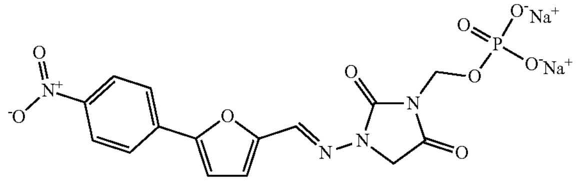

2a

Other dantrolene prodrugs include compounds of formula II

II

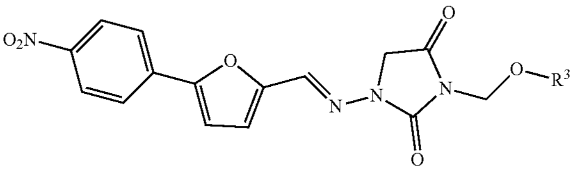

wherein $R_3$ is H, —C(O)—Z—N($R_4$)($R_5$), —C(O)Z—C(O)—OH, or —C(O)—NH—Y—$CH_2$—OC(O)—Z—C(O)—OH; Z is $C_{1-6}$alk; Y is arylene; $C_{1-6}$alkyl; $R_5$ is H or $C_{1-6}$alkyl; or $R_4$ and $R_5$, together with the nitrogen to which they are attached, form a heterocycloalkyl; as well as pharmaceutically acceptable salts thereof.

One aspect of the invention is directed to methods of treating COVID-19 in a subject. The subject may be clinically diagnosed with COVID-19. Criteria for diagnosing a subject with COVID-19 are known and include laboratory confirmation of a SARS-CoV-2 infection as determined using PCR, in combination with presentation of one or more COVID-19 symptoms. Other assays for determining SARS-CoV-2 infections can also be used. Symptoms of COVID-19 include mild to severe respiratory illness with symptoms of fever, cough, and shortness of breath. Some COVID-19 patients may develop pneumonia in one or both lungs. Some COVID-19 patients may develop multi-organ failure.

In some aspects, the subject may be suspected of having COVID-19, based on, for example, having experienced close contact with another person who has been clinically diagnosed with COVID-19 or who has been clinically diagnosed with a SARS-CoV-2 infection. Other subjects may be suspected of having COVID-19 based on the subject's symptom presentation.

In some aspects, the subject is treated for COVID-19 by administering to the subject dantrolene. In other aspects, the subject is treated for COVID-19 by administering to the subject a pharmaceutically acceptable salt of dantrolene, for example, dantrolene sodium. In some aspects, the subject is treated for COVID-19 by administering to the subject a dantrolene prodrug, for example, Compound 2. In some aspects, the subject is treated for COVID-19 by administering to the subject a salt of a dantrolene prodrug, for example, Compound 2a. Administration is preferably of a therapeutically effective amount of the dantrolene, pharmaceutically acceptable salt of dantrolene, dantrolene prodrug, or salt of a dantrolene prodrug. Therapeutically effective amounts include, for example, about 1 mg/kg to 10 mg/kg, administering daily, for one or more days. Particularly preferred amounts include about 1, 1.5, 2, 2.5, 3, 3.5, 4, 4.5, 5, 5.5, 6, 6.5, 7, 7.5, 8, 8.5, 9, 9.5, or about 10 mg/kg, administered daily, in one or more doses, for one or more days.

In some aspects, the administration results in at least a 1-point decrease in the subject's WHO Ordinal Scale score, as compared to the subject's WHO Ordinal Scale score at baseline. Methods of assessing WHO Ordinal Scale score are known in the art. In some aspects, the administration results in a 2-point decrease in the subject's WHO Ordinal Scale score, as compared to the subject's WHO Ordinal Scale score at baseline. In some aspects, the administration results in a 3-point decrease in the subject's WHO Ordinal Scale score, as compared to the subject's WHO Ordinal Scale score at baseline. In some aspects, the administration results in a 4-point decrease in the subject's WHO Ordinal Scale score, as compared to the subject's WHO Ordinal Scale score at baseline. In some aspects, the administration results in a 5-point decrease in the subject's WHO Ordinal Scale score, as compared to the subject's WHO Ordinal Scale score at baseline.

In some aspects, the administration results in an improvement, for example, an increase in the subject's Sequential Organ Failure Assessment daily score, as compared to baseline. Methods of assessing a subject's Sequential Organ Failure Assessment daily score are known in the art.

In some aspects, the administration results in a reduction of time to normalization of fever in the subject, as compared to the amount of time to normalization of fever in a control subject, for example, as compared to a subject who has only received standard of care treatment. In some aspects, the administration results in a reduction of fever in the subject treated for COVID-19. In other aspects, the administration results in a clinically significant reduction of fever in the subject. In some aspects, the administration results in a normalization of fever in the subject.

In some aspects, the administration results in a reduction of time to normalization of oxygen saturation in the subject, as compared to the amount of time to normalization of oxygen saturation in a control subject, for example, as compared to a subject who has only received standard of care treatment. In some aspects, the administration results in an increase of oxygen saturation in the subject. In other aspects, the administration results in a clinically significant increase in oxygen saturation in the subject. In other aspects, the administration results in normalization of oxygen saturation in the subject.

In yet other aspects, the administration results in improvement in one or more symptoms of COVID-19 in the subject. In other aspects, the administration results in a clinically significant improvement in one or more symptoms of COVID-19 in the subject.

Other aspects of the disclosure are directed to methods of inhibiting replication of SARS-CoV-2 in a subject. The subject may be clinically diagnosed with a SARS-CoV-2 infection. Criteria for diagnosing a subject with a SARS-CoV-2 infection are known and include laboratory confirmation as determined using PCR. Other assays for determining SARS-CoV-2 infections can also be used.

In some aspects, the subject may be suspected of having a SARS-CoV-2 infection, based on, for example, having experienced close contact with another person who has been clinically diagnosed with COVID-19 or who has been clinically diagnosed with a SARS-CoV-2 infection.

In some aspects, inhibition of SARS-CoV-2 replication in a subject is accomplished by administering to the subject dantrolene. In other aspects, inhibition of SARS-CoV-2 replication in a subject is accomplished by administering to the subject a pharmaceutically acceptable salt of dantrolene, for example, dantrolene sodium. In some aspects, inhibition of SARS-CoV-2 replication in a subject is accomplished by administering to the subject a dantrolene prodrug, for example, Compound 2. In some aspects, inhibition of SARS-CoV-2 replication in a subject is accomplished by administering to the subject a salt of a dantrolene prodrug, for example, Compound 2a. Administration is preferably of a therapeutically effective amount of the dantrolene, pharmaceutically acceptable salt of dantrolene, dantrolene prodrug, or salt of a dantrolene prodrug. Therapeutically effective amounts include, for example, about 1 mg/kg to 10 mg/kg, administering daily, for one or more days. Particularly preferred amounts include about 1, 1.5, 2, 2.5, 3, 3.5, 4, 4.5, 5, 5.5, 6, 6.5, 7, 7.5, 8, 8.5, 9, 9.5, or about 10 mg/kg, administered daily, in one or more doses, for one or more days.

Some aspects of the disclosure are directed to methods for inhibiting replication of SARS-CoV-2 in a host cell. Inhibition of viral replication can be determined by those skilled in the art. In these methods, replication is inhibited by administering dantrolene to the host cell. In other aspects, replication is inhibited by administering a pharmaceutically acceptable salt of dantrolene to the host cell, for example, dantrolene sodium. In some aspects, replication is inhibited by administering to the host cell a dantrolene prodrug, for example, Compound 2. In some aspects, replication is inhibited by administering to the host cell a salt of a dantrolene prodrug, for example, Compound 2a.

Some aspects of the disclosure are directed to methods for inhibiting entry of SARS-CoV-2 into a host cell. Inhibition of viral entry into a host cell can be determined by those skilled in the art. In these methods, viral entry is inhibited by administering dantrolene to the host cell. In other aspects, viral entry is inhibited by administering a pharmaceutically acceptable salt of dantrolene to the host cell, for example, dantrolene sodium. In some aspects, viral entry is inhibited by administering to the host cell a dantrolene prodrug, for example, Compound 2. In some aspects, viral entry is inhibited by administering to the host cell a salt of a dantrolene prodrug, for example, Compound 2a.

Some aspects of the disclosure are directed to methods for inhibiting SARS-CoV-2 virion maturation in a host cell. Inhibition of virion maturation in a host cell can be determined by those skilled in the art. In these methods, virion maturation is inhibited by administering dantrolene to the host cell. In other aspects, virion maturation is inhibited by administering a pharmaceutically acceptable salt of dantrolene to the host cell, for example, dantrolene sodium. In some aspects, virion maturation is inhibited by administering to the host cell a dantrolene prodrug, for example, Compound 2. In some aspects, virion maturation is inhibited by administering to the host cell a salt of a dantrolene prodrug, for example, Compound 2a.

Some aspects of the disclosure are directed to methods for release of SARS-CoV-2 from a host cell. Inhibition of release from a host cell can be determined by those skilled in the art. In these methods, viral release is inhibited by administering dantrolene to the host cell. In other aspects, viral release is inhibited by administering a pharmaceutically acceptable salt of dantrolene to the host cell, for example, dantrolene sodium. In some aspects, viral release is inhibited by administering to the host cell a dantrolene prodrug, for example, Compound 2. In some aspects, viral release is inhibited by administering to the host cell a salt of a dantrolene prodrug, for example, Compound 2a.

Some methods of the disclosure are directed to methods for reducing the infectivity of SARS-CoV-2. Reduction of infectivity can be determined by those skilled in the art. In these methods, infectivity is reduced by administering dantrolene to the host cell. In other aspects, infectivity is reduced by administering a pharmaceutically acceptable salt of dantrolene to the host cell, for example, dantrolene sodium. In some aspects, infectivity is reduced by administering to the host cell a dantrolene prodrug, for example, Compound 2. In some aspects, infectivity is reduced by administering to the host cell a salt of a dantrolene prodrug, for example, Compound 2a.

The following examples are provided to illustrate some of the concepts described within this disclosure. While each example is considered to provide specific individual embodiments of disclosure, none of the Examples should be considered to limit the more general embodiments described herein. In the following examples, efforts have been made to ensure accuracy with respect to numbers used (e.g. amounts, temperature, etc.) but some experimental error and deviation should be accounted for.

EXAMPLES

Example 1

Methodology

The study is a single-center, open-label, two-arm parallel study of dantrolene for the adjuvant treatment of COVID-19 administered intravenously (IV). In one treatment arm, dantrolene will be administered in conjunction with current standard of care following medical practice and procedures established for the in-hospital treatment of patients with COVID-19. In the second treatment arm, subjects will receive current standard of care following medical practice and procedures established for the in-hospital treatment of patients with COVID-19.

Following initial triage and primary assessment of a subject, the subject's baseline status will be documented. Once eligibility criteria and baseline status are obtained, administration of dantrolene will be initiated.

Group A: dantrolene, in addition to standard of care

Group B: standard of care only

Treatment Administration—Group A

Eligible COVID-19 subjects randomized to Group A will receive dantrolene (as RYANODEX, dantrolene sodium) as follows:

- A 1 mg/kg dose will be administered as IV push approximately every 12 hours for 2 consecutive days (Study Day 1 and Day 2).
- On Day 3 of the Study, subjects showing adequate tolerability to 1 mg/kg dose will start receiving 2 mg/kg dose as IV push approximately every 12 hours for the remainder of the study (Study Day 3 to Day 14, inclusive). Adequate tolerability is defined as lack of clinically significant adverse reactions that may have a negative impact on the subject's overall status that are not secondary to COVID-19, any other underlying condition or concomitant medication.
- If a patient does not show adequate tolerability to the 2 mg/dose, the subject will be discontinued from the study.
- Each subject participating in the study will receive up to 4 (four) 1 mg/kg doses (Days 1-2) and up to 24 (twenty four) doses of 2 mg/kg (Days 3-14), each administered as an IV push (up to a minute).

Subjects receiving dantrolene will continue to receive all other treatments as prescribed, with the exception of treatments included in the Exclusion Criteria. Assessment of vital signs (blood pressure, heart rate, respiratory rate, body temperature) should be clearly recorded prior to and within 10 minutes after administration of each dose.

Group B

Patients randomized to Group B will receive standard of care, following acceptable medical practice.

Study Phases

The study will include 2 phases: Screening and Treatment.

During the Screening Phase, eligibility and baseline assessment will be performed. Informed Consent will be obtained prior to initiation of study procedures.

After determination of eligibility and obtaining Informed Consent, eligible patients will be randomized to Group A or Group B and the Treatment Phase will be initiated and will proceed with administration of Study Drug as indicated above to Group A Non-eligible subjects will receive medical assistance as deemed necessary by the attending physician following accepted medical practices.

Stopping the Study Drug

If the subject demonstrates clinically significant signs/symptoms of dantrolene toxicity, the study drug should he stopped. Dantrolene toxicity may include muscular weakness and alterations in the state of consciousness (e.g., lethargy, sedation), vomiting, diarrhea, and crystalluria, which are not attributable to other cause, such as progression of COVID-19, other underlying conditions (e.g., sepsis, hypoxia, uncontrolled diabetes) and/or concomitant medications (e.g., sedatives, antibiotics, antipyretics). The study drug can be stopped at any time.

Diagnosis and Main Criteria for Inclusion

Male or non-pregnant female subjects will be entered into the study if they are diagnosed with COVID-19 and meet all the following criteria at Screening:

- At least 18 years of age.
- Willing and able to provide written informed consent prior to performing study procedures, or an authorized representative is willing and able to provide consent on behalf of the patient if he/she is unable to do so.
- COVID-19 severity score 3-5 according to the WHO Ordinal Scale of Severity
- COVID-19 symptoms onset within 7 days prior to Screening.
- Hospitalized patient.
- Has laboratory-confirmed SARS-CoV-2 infection as determined by PCR, or other commercial or public health assay within 48 hours prior to Screening.
- Febrile defined as temperature ≥36.6° C. armpit, ≥37.2° C. oral, or ≥37.8° C. rectal documented at least within 48 hours of consent.

Male or non-pregnant female subjects will be excluded from entering this study if they meet any of the following criteria at Screening:

Participation in any other clinical trial of an experimental treatment for COVID-19.

Alanine Aminotransferase (ALT) or aspartate aminotransferase (AST) >5× upper limit of normal (ULN).

Pregnant women or women who are breastfeeding.

Presence of comorbidities that imply a poor prognosis (according to clinical judgment).

Allergy to dantrolene.

Dosage and Mode of Administration

Ryanodex: (dantrolene sodium) for injectable suspension; 250 mg/vial to be reconstituted with 5 mL of sterile water for injection (without a bacteriostatic agent) to yield a 50 mg/mL suspension; to be administered as a rapid IV push of 1 mg/kg or 2 mg/kg, as described in the protocol.

Efficacy will be evaluated on criteria including:

World Health Organization (WHO) Ordinal Scale of Severity score.

Sequential Organ Failure Assessment (SOFA) score.

Length of time to normalization of fever (fever normalization as defined by temperature <36.6° C. armpit, <37.2° C. oral, or <37.8° C. rectal sustained for minimum of 24 hours).

Length of time to normalization of oxygen saturation (oxygen normalization as defined by peripheral capillary oxygen saturation (SpO2)>94% sustained for at least 24 hours).

Change in clinical status at Day 14 using the WHO Ordinal Scale (1-8 score), compared to Baseline.

1: Ambulatory. No limitations of activities

2: Ambulatory limitation of activities

3: Hospitalized, Mild Disease. No oxygen therapy

4: Hospitalized, Mild Disease. Oxygen by mask or nasal prongs

5: Hospitalized, Severe Disease. Non-invasive ventilation or high-flow oxygen

6: Hospitalized, Severe Disease. Intubation and mechanical ventilation

7: Hospitalized, Severe Disease. Ventilation+additional organ support (pressors, renal replacement therapy, extracorporeal membrane oxygenation)

8: Death

Change in clinical status at Day 5 and Day 10 using the WHO Ordinal Scale (1-8 score), compared to Baseline.

Time to a 1-point decrease in the WHO Ordinal Scale score.

Change in Sequential Organ Failure Assessment (SOFA) daily score (Days 1-14) compared to Baseline.

Length of time to normalization of fever ((fever normalization as defined by temperature <36.6° C. armpit, <37.2° C. oral, or <37.8° C. rectal sustained for minimum of 24 hours).

Length of time to normalization of oxygen saturation (oxygen normalization as defined by peripheral capillary oxygen saturation (SpO2)>94% sustained for at least 24 hours).

Safety will be evaluated and will include measurement and observation of (if any):

Vital signs (heart rate, blood pressure, respiratory rate, body temperature)

Clinical laboratory tests (hematology and blood chemistry)

ECG monitoring

Oxygen saturation

Physical exam

Example 2

Dantrolene concentrations were tested: 5, 10, 20, 30, 40, 50 and 100 μM (as RYANODEX, dantrolene sodium).

Testing against a SARS-CoV-2 virus, represents the etiologic agent of the COVID-19 global pandemic. Testing was via a standard virus neutralization (VN) assay, which assessed ability to neutralize SARS-CoV-2.

Virus Neutralization (VN) Assay. The VN assay was performed using Vero E6 cells which are susceptible to SARS-CoV-2 infection. The cells were seeded into 96-well plates one (1) to three (3) days prior to VN assay, and were incubated at 37° C. and 5% $CO_2$. On the day of assay, the monolayer of Vero E6 cells was at least 70% to 80% confluent in order to run the VN. The preparation of the compound for VN was performed the day of assay. The compound was diluted with serum-free media to the desired starting concentration (1:10) and then serially diluted 2-fold in serum-free media.

Standardization of the virus required that a TCID50 had previously been run to determine the concentration of infectious virus particle per mL of virus stock. Using the TCID50 titer, calculations were performed to define how much serum-free media to add to the virus stock to yield 1e2 TCID50/mL. Once the standardized virus was made, an equal volume of it was added to the deep 96-well plate containing the diluted compound samples. Incubation was maintained for at least one hour. The virus/compound mixture was then transferred from the deep 96-well racks into the appropriate Vero-seeded 96-well plates. After this addition, the plates were returned to the 37° C. and 5% $CO_2$ incubator for three (3) to five (5) days to six (6) days. After the incubation period, the wells were observed under a phase contrast inverted scope and were scored for the presence or absence of SARS-CoV-2 cytopathic effects (CPE) in the cells. The titer was the inverse of the last dilution of dantrolene that inhibits the viral infection (cells that do not display CPE), i.e., the lowest effective titer was the last dilution of dantrolene that consistently inhibited viral infection (cells do not display CPE) across all time points.

There were several controls present on each plate for the VN assay. First, there was a compound control that lacked virus to ensure that the compound itself did not cause CPE; this control was performed using the lowest dilution of compound in the series (usually 1:10) and additional serial dilutions at the test concentrations. There were also negative control wells (without compound or virus) to verify that the serum-free media did not cause CPE. Also, a back-titer of the virus was performed which acted as a positive CPE control for the virus, and it served to verify that the titer of the standardized virus was within acceptable range. Results from the samples on that plate were considered valid if all of these controls met their acceptance criteria.

Without wishing to be bound to any particular theory, it is believed that dantrolene modulates intracellular $Ca^{2+}$ including by mechanisms not previously reported, thereby affecting the ability of the SARS-CoV-2 virus to, for example, infect cells, replicate, mature, create virions, or release from cells.

Example 3

Dantrolene concentrations were tested: 5, 10, 20, 30, 40, 50 and 100 μM (as RYANODEX, dantrolene sodium).

Testing against a SA RS-CoV-2 virus; represents the etiologic agent of the COVID-19 global pandemic. Testing was via a standard virus neutralization (VN) assay, which assessed ability to neutralize SARS-CoV-2.

Virus Neutralization (VN) Assay. The VN assay was performed using Vero E6 cells, an African green monkey cell line, which are susceptible to SARS-CoV-2 infection.

Vero E6 cells were cultured in growth media (Dulbecco's Modified Eagle Medium supplemented with 5% FBS (fetal bovine serum), Glutamax, and PSN (penicillin, streptomycin, and neomycin)). The cells were seeded into deep 96-well plates one day prior to the VN assay and incubated at 37° C. and 5% $CO_2$ to allow the cells to grow to 70% confluency. Each of the samples and controls were performed in triplicate.

The preparation of RYANODEX for VN was performed the day of assay. RYANODEX was reconstituted with 5 ml, of sterile water for injection, as described in the RYANODEX Prescribing Information, to prepare an initial stock having a dantrolene concentration of 50 mg/mL. The stock was further diluted to a dantrolene concentration of 100 μM using cell growth media and then serially diluted to 50, 40, 30, 20, 10 and 5 μM. The dilutions were preincubated on cells for 60 minutes prior to addition of virus.

Standardization of the virus required that a Medium Tissue Culture Infectious Dose (TCID50) have been previously performed to determine the concentration of infectious virus particle per mL of virus stock, using procedures known in the art. See, e.g., Reed & Muench, (1938) A simple method of estimating fifty percent endpoints, The American Journal of Hygiene. 27: 493-497; World Health Organization, Laboratory Procedures, Serological detection of avian influenza A(H7N9) infections by microneutralization assay, May 23, 2013 Using the TCID50 titer, calculations were performed to define how much serum-free media to add to the virus stock to yield 1e2 TCID50/mL. Once the standardized virus was made, an equal volume of it was added to the deep 96-well plate containing the diluted compound samples.

Virus was added to the appropriate wells and incubated with cells and compound for 2 hours. The cells were then washed 3 times with fresh media and 100 μL/well of fresh media was added to all wells and further incubated for 6 days. During the incubation period, the wells were observed under a phase contrast inverted scope and were scored for the presence or absence of SARS-CoV-2 cytopathic effects (CPE) in the cells. The titer was the inverse of the last dilution of dantrolene that inhibits the viral infection (cells that do not display CPE), i.e., the lowest effective titer was the last dilution of dantrolene that consistently inhibited viral infection (cells do not display CPE) across all time points.

There were several controls present on each plate for the VN assay. First, there was a dantrolene control that included RYANODEX alone at the test concentrations without virus to ensure that dantrolene itself at the tested concentrations does not cause CPE. There were also negative control wells (without RYANODEX or virus) to verify that the serum-free media did not cause CPE. Also, a back-titer of the virus that included 100 μL TCID50/well of virus was performed which acted as a positive CPE control for the virus, and it served to verify that the titer of the standardized virus was within acceptable range. Results from the samples on that plate were considered valid if all of these controls met their acceptance criteria.

The analysis of the neutralization assay revealed that the highest dantrolene concentrations (50 and 100 μM dilution) showed cytopathic effects on Days 2 and 4, in both infected cells and uninfected controls, as expected. The 50 μM dilution had rebound cell growth on Day 6 post-infection, but it was decreased compared to the lower dilutions. The uninfected controls displayed the same cytotoxicity profile as the infected replicates at these higher dantrolene concentrations.

On Day 2 post-infection no CPE was observed in any wells containing RYANODEX. On Day 4 and Day 6 post-infection, no CPE was observed in cells incubated with 20-40 μM of dantrolene. CPE was observed in 2 of 3 replicates at Days 4 and 6 post-infection with 10 μM of dantrolene, but no CPE was observed at Day 2. At the 5 μM concentration of dantrolene, CPE was observed in 1 of 3 replicates at Days 4 and 6 post infection, but no CPE was observed at Day 2 at this dantrolene concentration. See Table.

TABLE

| Dilution | Day 2 Read | Day 4 Read | Day 6 Read |
|---|---|---|---|
| 100 μM | 3/3 wells had >90% CPE | 3/3 wells had >90% CPE | 3/3 wells had >90% CPE |
| 50 μM | 3/3 wells had sparce confluency | 3/3 wells had sparce confluency | 3/3 wells had sparce confluency but greater than Day 4 |
| 40 μM | 3/3 wells had No CPE | 3/3 wells had No CPE | 3/3 wells had No CPE |
| 30 μM | 3/3 wells had No CPE | 3/3 wells had No CPE | 3/3 wells had No CPE |
| 20 μM | 3/3 wells had No CPE | 3/3 wells had No CPE | 3/3 wells had No CPE |
| 10 μM | 3/3 wells had No CPE | 2/3 wells had >90% CPE | 2/3 wells had >90% CPE |
| 5 μM | 3/3 wells had No CPE | 1/3 wells had >90% CPE | 1/3 wells had >90% CPE |

CPE = cytopathic effects

All uninfected controls remained healthy and did not display any CPE throughout the 6-day post-infection incubation period. It was concluded that the minimum inhibitory concentration of dantrolene is 20 μM, though lower concentrations of 10 and 5 μM also showed anti-viral activity. No cytopathic effects (indicating no virus growth) were observed with the 20 and 40 μM dantrolene concentrations at all timepoints. Cytotoxic effects were only observed at the 2 highest dantrolene concentrations (100 and 50 μM), both with or without virus. In contrast, at the lower dilutions (<50 μM dantrolene) uninfected Vero E6 cells showed good cell viability. The control cells infected with the virus but without RYANODEX all had CPE, evidencing viral growth.

In summary, the VN assay demonstrated the in vitro antiviral activity and lack of cytotoxicity of RYANODEX at dantrolene concentrations compatible with human plasma levels observed after administration of the recommended doses of RYANODEX.

Without wishing to be bound to any particular theory, it is believed that dantrolene modulates intracellular $Ca^{2+}$, including by mechanisms not previously reported, thereby affecting the ability of the SARS-CoV-2 virus to, for example, infect cells replicate, mature, create virions, or release from cells.

What is claimed:

1. A method of treating COVID-19 in a subject comprising administering to the subject dantrolene or a pharmaceutically acceptable salt thereof, or by administering a compound of Formula I:

I

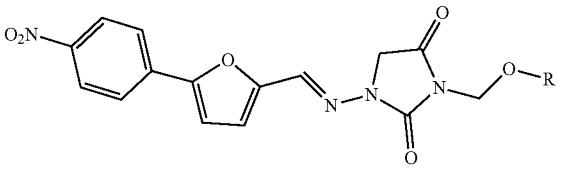

wherein R is —P(O)(OH)$_2$ or —P(O)(OR$_1$)(OR$_2$); $R_1$ is H, —$C_{1-26}$alkyl, aryl, $C_{1-6}$alkC(O)O—$C_{1-26}$alkyl, —$C_1$alkOC(O)$C_{1-26}$alkyl, or $C_1$alkOC(O)O$C_{1-26}$alkyl; and $R_2$ is —$C_{1-26}$alkyl, aryl, $C_{1-6}$alkC(O)O—$C_{1-26}$alkyl, —$C_1$alkOC(O)$C_{1-26}$alkyl, or $C_1$alkOC(O)O$C_{1-26}$alkyl; or a pharmaceutically acceptable salt thereof.

2. The method of claim 1, comprising administering dantrolene to the subject.

3. The method of claim 1, comprising administering a pharmaceutically acceptable salt of dantrolene to the subject.

4. The method of claim 1, comprising administering dantrolene sodium to the subject.

5. The method of claim 1, wherein the administration results in at least a 1-point decrease in the subject's WHO Ordinal Scale score, as compared to baseline.

6. The method of claim 1, wherein the administration results in an improvement in the subject's Sequential Organ Failure Assessment daily score, as compared to baseline.

7. The method of claim 1, wherein the administration results in a reduction of time to normalization of fever in the subject, as compared to the amount of time to normalization of fever in a control subject.

8. The method of claim 1, wherein the administration results in a reduction of time to normalization of oxygen saturation in the subject, as compared to the amount of time to normalization of oxygen saturation in a control subject.

9. A method for inhibiting replication of SARS-CoV-2 in a subject comprising administering to the subject dantrolene, or a pharmaceutically acceptable salt thereof, or by administering a compound of Formula I:

I

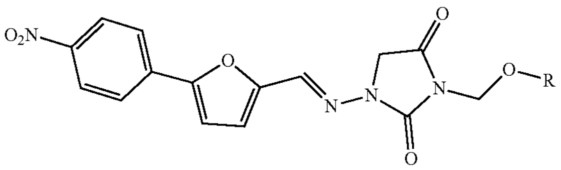

wherein R is —P(O)(OH)$_2$ or —P(O)(OR$_1$)(OR$_2$); $R_1$ is H, —$C_{1-26}$alkyl, aryl, $C_{1-6}$alkC(O)O—$C_{1-26}$alkyl, —$C_1$alkOC(O)$C_{1-26}$alkyl, or $C_1$alkOC(O)O$C_{1-26}$alkyl; and $R_2$ is —$C_{1-26}$alkyl, aryl, $C_{1-6}$alkC(O)O—$C_{1-26}$alkyl, —$C_1$alkOC(O)$C_{1-26}$alkyl, or $C_1$alkOC(O)O$C_{1-26}$alkyl; or a pharmaceutically acceptable salt thereof.

10. The method of claim 9, comprising administering dantrolene to the subject.

11. The method of claim 9, comprising administering a pharmaceutically acceptable salt of dantrolene to the subject.

12. The method of claim 9, comprising administering dantrolene sodium to the subject.

13. A method for inhibiting replication of SARS-CoV-2 in a host cell, for inhibiting entry of SARS-CoV-2 into a host cell, for inhibiting SARS-CoV-2 virion maturation in a host cell, or for inhibiting release of SARS-CoV-2 from a host cell comprising administering to the host cell dantrolene, or a pharmaceutically acceptable salt thereof, or by administering a compound of Formula I:

I

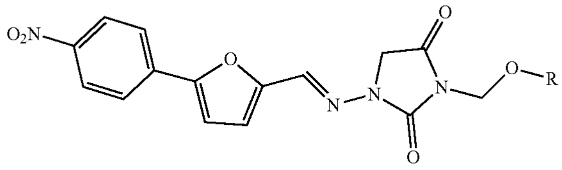

wherein R is —P(O)(OH)$_2$ or —P(O)(OR$_1$)(OR$_2$); $R_1$ is H, —$C_{1-26}$alkyl, aryl, $C_{1-6}$alkC(O)O—$C_{1-26}$alkyl, —$C_1$alkOC(O)$C_{1-26}$alkyl, or $C_1$alkOC(O)O$C_{1-26}$alkyl; and $R_2$ is —$C_{1-26}$alkyl, aryl, $C_{1-6}$alkC(O)O—$C_{1-26}$alkyl, —$C_1$alkOC(O)$C_{1-26}$alkyl, or $C_1$alkOC(O)O$C_{1-26}$alkyl; or a pharmaceutically acceptable salt thereof.

14. The method of claim 13, comprising administering dantrolene to the host cell.

15. The method of claim 13, comprising administering a pharmaceutically acceptable salt of dantrolene to the host cell.

16. The method of claim 13, comprising administering dantrolene sodium to the host cell.

17. A method for reducing the infectivity of SARS-CoV-2 by administering to a host cell dantrolene, or a pharmaceutically acceptable salt thereof, or by administering a compound of Formula I:

I

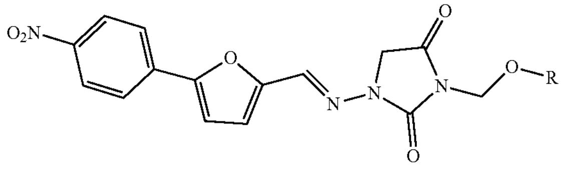

wherein R is —P(O)(OH)$_2$ or —P(O)(OR$_1$)(OR$_2$); $R_1$ is H, —$C_{1-26}$alkyl, aryl, $C_{1-6}$alkC(O)O—$C_{1-26}$alkyl, —$C_1$alkOC(O)$C_{1-26}$alkyl, or $C_1$alkOC(O)O$C_{1-26}$alkyl; and $R_2$ is —$C_{1-26}$alkyl, aryl, $C_{1-6}$alkC(O)O—$C_{1-26}$alkyl, —$C_1$alkOC(O)$C_{1-26}$alkyl, or $C_1$alkOC(O)O$C_{1-26}$alkyl; or a pharmaceutically acceptable salt thereof.

18. The method of claim 17, comprising administering dantrolene to the host cell.

19. The method of claim 17, comprising administering a pharmaceutically acceptable salt of dantrolene to the host cell.

20. The method of claim 17, comprising administering dantrolene sodium to the host cell.

21. The method of claim 1, wherein the compound of Formula I is:

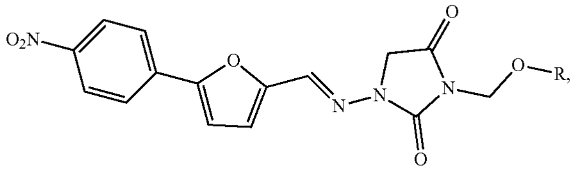
wherein R is —$P(O)(OH)_2$.
22. The method of claim 9, wherein the compound of formula I is:
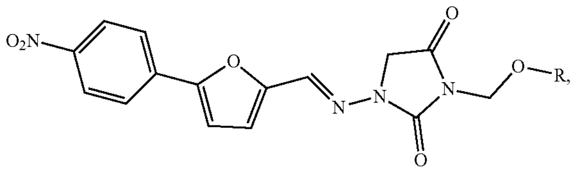
wherein R is —$P(O)(OH)_2$.
23. The method of claim 13, wherein the compound of Formula I is:
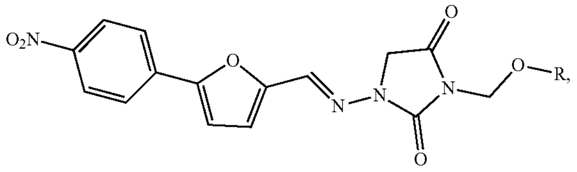
wherein R is —$P(O)(OH)_2$.
24. The method of claim 17, wherein the compound of Formula I is:
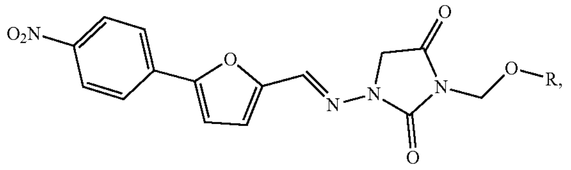
wherein R is —$P(O)(OH)_2$.
* * * * *